United States Patent [19]
Jasen et al.

[11] Patent Number: 5,284,469
[45] Date of Patent: Feb. 8, 1994

[54] NASAL DRESSING HOLDER

[75] Inventors: Marianne Jasen, Amherst; Suzanne Lewandowski, DePew, both of N.Y.

[73] Assignee: Dale Medical Products, Inc., Plainville, Mass.

[21] Appl. No.: 790,589

[22] Filed: Nov. 8, 1991

[51] Int. Cl.$^5$ .............................................. A61F 5/00
[52] U.S. Cl. ................................. 602/17; 128/858; 128/866
[58] Field of Search ............... 128/875, 876, 858, 866, 128/DIG. 15, DIG. 26, 848, 845; 606/204.15, 205.25, 205.35, 205.45; 602/17; 2/338, 2, 46

[56] References Cited

U.S. PATENT DOCUMENTS

| | | | |
|---|---|---|---|
| 587,193 | 7/1897 | Ferdy . | |
| 862,794 | 8/1907 | Black | 606/204.35 |
| 1,497,858 | 6/1924 | Lewis | 606/204.35 |
| 1,593,216 | 7/1926 | Lewis | 606/204.35 |
| 1,629,460 | 5/1927 | Skinner | 606/204.35 |
| 1,643,090 | 9/1927 | Rogers | 606/204.35 |
| 2,241,292 | 5/1941 | Burke | 123/132 |
| 3,540,440 | 11/1970 | Andreas | 606/204.35 |
| 3,672,362 | 6/1972 | Basché | 606/204.35 |
| 4,402,314 | 9/1983 | Goode | 606/204.35 |
| 4,694,823 | 9/1987 | Young | 606/204.35 |
| 4,836,200 | 6/1989 | Clark | 128/207.18 |

FOREIGN PATENT DOCUMENTS 3048224 12/1980 Fed. Rep. of Germany .

OTHER PUBLICATIONS

D. Martin, "No Tape After Nasal Surgery," Nursing '91, Jul. 1991.

Primary Examiner—Michael A. Brown
Attorney, Agent, or Firm—Wolf, Greenfield & Sacks

[57] ABSTRACT

A nasal dressing holder consisting of an elastic band positionable under the nose for holding a nasal dressing and packing in place, a pair of non-stretchable straps on either side of the band positionable across the cheeks, and a pair of thin elastic loops which are positionable around the ears for holding the device in place. A double-sided hook tab is positionable between a folded end of the strap and another portion of the strap and is releasably attachable to loop material on the strap, to enable releasable and adjustable attachment of the device to a patient. The tension applied to the dressing and packing can be varied by adjusting the folded connection between the strap and the loop.

19 Claims, 2 Drawing Sheets

NASAL DRESSING HOLDER

BACKGROUND OF THE INVENTION

This invention concerns a device for holding a nasal dressing and nasal packing in position, and more particularly a holder which is adjustable, easy to use, and does not cause skin irritation or pain.

Presently, in any surgery which involves the nasal or sinus areas, a 4×4" gauze dressing, sometimes called a moustache dressing, is folded and placed against the nostrils to catch drainage. Typically, this dressing is necessary for 2-3 days. On the first day, this dressing may have to be changed as often as eight times, depending on the amount of drainage.

In current practice, these dressings are typically held in place with tape. This tape is applied to the face, even though the patient's eyes, nose, and face are swollen and extremely sensitive. Every time the dressing is changed, the tape must be lifted off the skin, causing pain to the patient. In addition, the use of tape can cause tape burns, and possibly increase edema and redness of the face, as well as cause allergic reactions in some patients.

Another known practice is to stretch a rubber band under the nose and tape both ends of the band to the face. However, this does not avoid the problems of using tape and may not hold the dressing or packing securely.

Thus, a need exists for a nasal dressing holder which does not cause further irritation and pain to the patient.

Often times after surgery, nasal packing is put in each nostril to apply pressure and promote closure of the wound. The amount of time the packing remains in the nose varies depending on the type of surgery. A need exists to provide pressure to hold the packing in place, without causing the patient further irritation and pain.

Other problems which a nasal dressing holder should solve are preventing the dressing from falling down as it gets wet, and holding the dressing and packing securely in place when the patient moves his head from side to side.

It would also be desirable to reduce the nursing time required to change the dressing. Because of the frequency of changes required during a patient's stay in the post anesthesia recovery unit, the changing procedure should be kept as convenient and short as possible.

Still further, almost all nasal surgery patients go home with the dressing applied and are given extra supplies and instructions for changing the dressing at home. Thus, it would be desirable to provide a dressing holder which can be easily and properly used by the patient himself.

These problems are solved by the nasal dressing holder of this invention.

SUMMARY OF THE INVENTION

In accordance with this invention, a nasal dressing holder is provided which includes an elastic band positionable under the nose, a pair of substantially inelastic straps attached to opposite ends of the band and positioned to lie along the patient's cheeks, and a pair of elastic loops attached to the other ends of the strap to encircle the patient's ears for releasably attaching the device to the patient's head, and wherein the length of the straps is adjustable to accommodate all size patients and to vary the amount of tension applied by the band.

In applicant's preferred embodiment, a folded portion is provided at the end of each strap for engaging the loop, and the folded strap portion is adjustably and releasably engaged with another portion of the strap by intermeshing hook and loop members.

The holder does not involve attachment to any of the sensitive areas of the face, and thus eliminates the pain and irritation problems of the prior art tape method.

Furthermore, the holder is simple to use. To change a dressing, the band can be pulled away slightly from the nasal area to enable removal of the used dressing and insertion of a new dressing. Alternatively, one or both of the loops can be removed from the ears, a new dressing applied, and the holder reapplied by stretching the loops over the ears. As a further alternative, one or both of the adjustable hook and loop fastening members can be released to permit changing of the dressing.

Still further, the holder enables the user to apply a variable amount of tension against the nose to hold the dressing and packing in place. This is accomplished by adjusting the intermeshing hook and loop members on either strap, which can be done while the device is positioned on the patient. Further, the patient is free to move his head from side to side while the dressing is held securely in position.

These and other benefits of this invention are more clearly described in the following detailed description of a preferred embodiment.

DETAILED DESCRIPTION

Figure 1:
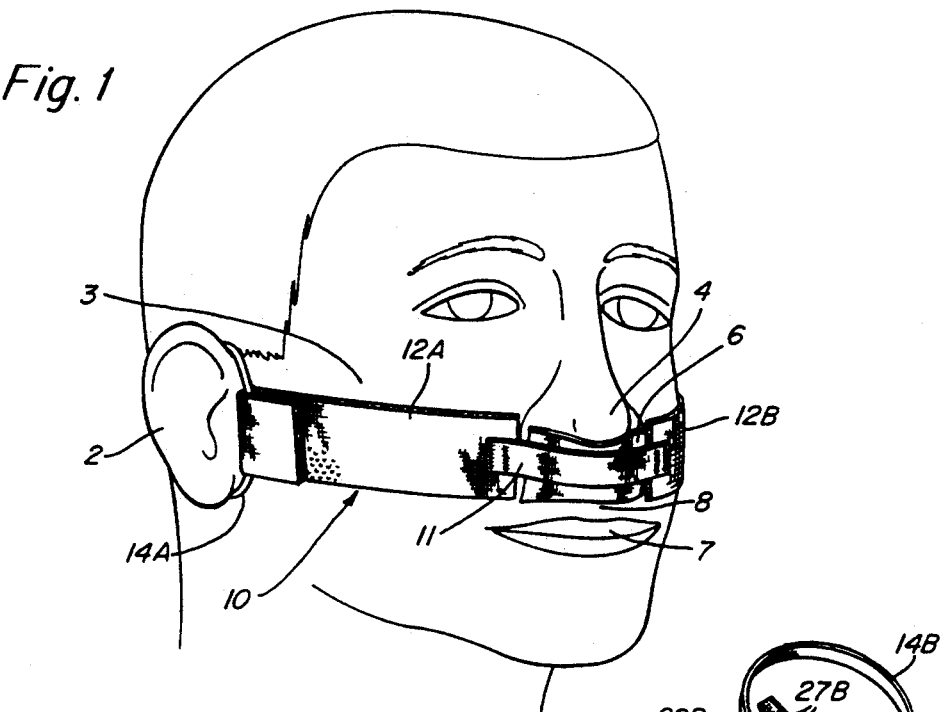
FIG. 1 is a front perspective view of a nasal holder of this invention positioned on a patient's head.

As shown in FIG. 1, the nasal dressing holder 10 of this invention consists of a central elastic band 11 positionable below the nose and above the lip for holding a dressing 6 in place, a pair of non stretchable straps 12A, 12B on either side of the band positionable across the patient's cheeks 3, and a pair of elastic loops 14A, 14B extending from the straps and positionable around the patient's ears 2 for holding the device in place. A double sided hook fastener 23 (see FIGS. 2-3) is positionable between a folded end and midportion 18 of each strap and is releasably attachable to loops 22 on the outer surface of the strap, to provide a variable amount of tension and to enable releasable and adjustable attachment of the device to the patient.

The elastic band 11 is positionable over an area 8 below the nose 4 and above the upper lip 7. FIG. 1 shows dressing 6 over each nostril and firmly held in place by band 11, which stretches below both nostrils and terminates adjacent either side of the nose. Band 11 is preferably a covered elastic member about ⅞" in width and 2¾" in length (unstretched), and is attached by one or two rows of stitching 26A, 26B to first ends 16A, 16B of straps 12A, 12B. Preferably, band 11 has a looped nylon material on its inner surface to frictionally engage the dressing and hold it more securely in position. The packing is placed further up in the nostrils and is not shown.

The straps 12A, 12B each have a first end 16 disposed adjacent the nose and a second end 17 which is adjustably folded back adjacent the ear 2. Each strap 12 is non-stretchable and preferably is made of a three layer construction, including a hypo-allergenic cotton inner layer 20 positionable against the face, a middle foam layer 21 for comfort, and an outer nylon layer 19 for strength with loops 22 for attachment to the hook tab 23. In a preferred embodiment, each strap 12A and 12B is about ⅜" wide and 5½" in length (unfolded).

The elastic loops 14A, 14B are releasably positionable around the ears 2 for holding the device on the patient's head. Preferably, a narrow covered elastic band, of ⅛" width and 2½" diameter (unstretched), is provided. The loop may be formed by overlapping opposing ends 27 of a 5½" length of elastic, and joining the ends with stitching 28 (see FIG. 2). The narrow elastic band 14 is designed to comfortably fit around the ear without undue tension, enabling the device to be worn for many hours and days without patient discomfort or irritation.

Figure 2:
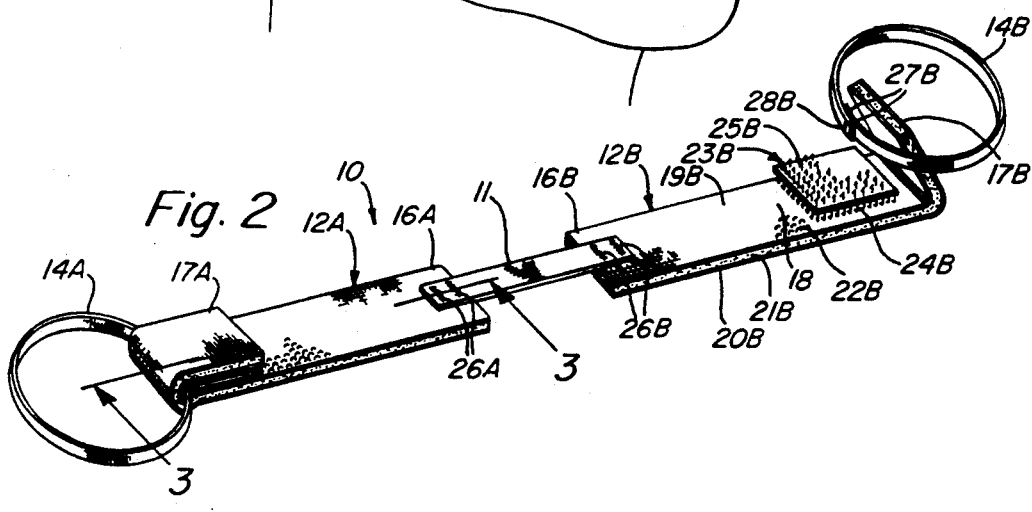
FIG. 2 is a top perspective view of the nasal dressing holder, showing the adjustable fastener between the loop and strap at one end.
Figure 3:
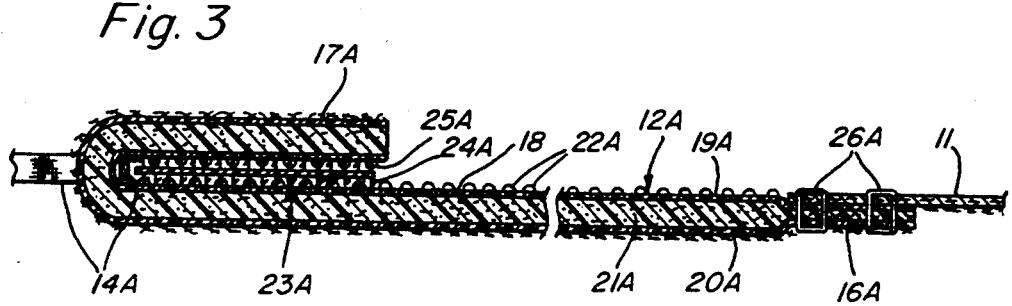
FIG. 3 is a partial cross sectional view taken along the section lines 3 3 of FIG. 2, showing the adjustable fastener.

The double-sided hook tab 23, as shown in FIGS. 2-3, has a first side 24 with hooks which engage the loops 22 on a central or midportion 18 of the strap 12, and a second side 25 with hooks which engage the loops 22 on the folded end 17 of the strap 12. Tab 23 may be removably positioned along the length of strap 12 in order to adjust for various patient sizes, or to vary the tension applied by band 11 to the dressing and patient's nasal area. Preferably, a double sided Velcro hook fastener is provided as tab 23 (VELCRO is a registered trademark of VELCRO USA Inc., Manchester, N.H.).

To use the device, the dressing 6 is first applied against the nostrils and the device is then applied to the patient by positioning band 11 over the dressing in area 8 below the nose 4 and above the upper lip 7 and positioning the loops 14 around the patient's ears 2. The size adjustment and/or the amount of tension applied by band 11 to the dressing or packing may be adjusted while the device is on the patient by pulling folded end 17 away from tab 23 and readjusting the length of folded end 17, and if necessary repositioning tab 23 along the length of strap 12. Preferably, the length of both straps 12A, 12B are adjusted equally in this fashion to keep the band 11 centered under the patient's nose and to ensure even pressure distribution. Alternatively, the device can be removed from the patient and the folded ends 17 adjusted in length. The excess strap material can be cut and discarded.

To change the dressing, the band 11 can be simply pulled away from the nose and a new dressing inserted, while leaving the device on the patient. Alternatively, one or both loops 14 can be stretched and removed from the ears while the dressing or packing is changed. As a further alternative, one or both of the folded ends 17 can be released from tabs 23, while leaving the loops 14 on the ears, in order to change the dressing.

It may be desirable to position band 11 relatively low and resting adjacent the upper lip area 8 when securing the dressing for drainage purposes, and relatively high, against the nostrils, when applying pressure.

Figure 4:
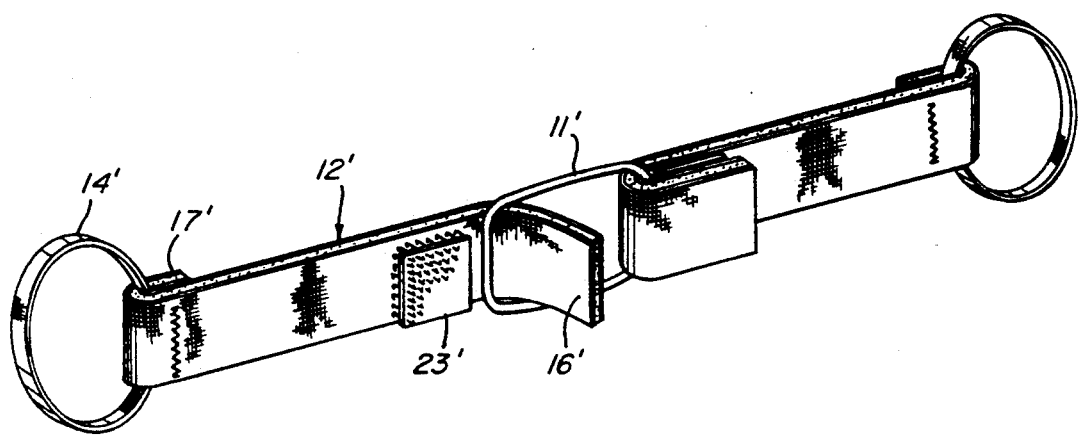
FIG. 4 is a top perspective view of an alternative embodiment, having adjustable fasteners between a central looped band and support straps.

While a preferred embodiment has been described herein, it is understood that modifications may be made within the scope of this invention. For example, adjustability may be additionally or alternatively be provided at the first end 16 of the strap 12, adjacent the band 11. Thus, as shown in FIG. 4, end 16 may be folded (similar to end 17 in FIG. 2) around a looped band 11' (instead of the single band 11 shown in FIG. 2) and an adjustable hook tab 23' provided to attach end 16' to the strap 12', while ear loops 14' are fixed between the folded and sewn ends 17'. Still further, some other adjustable fastener may be provided between end 16 and band 11. In addition, other types of fasteners may be used to join band 11 and straps 12, and to join the ends of loop 14, such as metal or plastic fasteners. Furthermore, the dimensions and lengths of the various components may be altered to better fit a particular type of patient or hold a particular type of dressing.

While certain preferred embodiments of the invention have hereinbefore been described, it will be appreciated that variations and equivalents thereof will be perceived by those skilled in the art, which are nevertheless within the scope of the invention as defined by the claims appended hereto.

We claim:

1. A nasal dressing holder for releasable attachment to a patient comprising:
    an elongated central elastic band having opposing ends, the band being of a first width sized to fit beneath a patient's nose and hold a dressing against the nostrils without engaging the patient's upper lip;
    a pair of substantially inelastic support straps having first ends attached to the opposing ends of the central band and adapted to lie against the patient's cheeks;
    a pair of elastic ear loops, one attached to a second end of each support strap and adapted to encircle a different one of the patient's ears for releasably attaching the holder to the patient's head; and
    releasable strap-length adjusting means permitting release of the central band from beneath the patient's nose to change a dressing and to adjust the length of each support strap to vary the amount of tension applied by the band for holding the nasal dressing in place.

2. The holder of claim 1, wherein the strap-length adjusting means comprises a folded portion at the second end of each strap in which the ear loop is positioned, and releasable and adjustable engaging means are provided for securing the folded portion to another portion of the support strap.

3. The holder of claim 2, wherein the releasable and adjustable engaging means are intermeshing hook and loop members.

4. The holder of claim 3, wherein an outer surface of each support strap is provided with the loop members and the hook members are provided on both sides of a pair of tabs which are each releasably attachable to the folded portion and another portion of the support strap.

5. The holder of claim 1, wherein the ear loops are releasably attachable to the second ends of the support straps.

6. The holder of claim 1, wherein the support straps are releasably attachable to the central band.

7. The holder of claim 1, wherein the support straps have an inner layer of cotton, a middle layer of foam, and an outer layer of nylon loops.

8. The holder of claim 1, wherein the first ends of the support straps are stitched to the central band.

9. The holder of claim 1, wherein the strap-length adjusting means comprises a pair of tab portions attached to the opposing ends of the support strap and having releasable and adjustable engaging means for attachment to the support straps.

10. The holder of claim 9, wherein the releasable and adjustable engaging means are intermeshing hook and loop members.

11. The holder of claim 10, wherein an outer surface of each support strap is provided with loop members and the hook members are provided on the tabs.

12. The holder of claim 1, wherein the central band is a loop and the strap-length adjusting means is a folded portion at the first end of each support strap in which a portion of the central loop is positionable, and releasable and adjustable engaging means are provided for securing each folded portion to another portion of the support strap.

13. The holder of claim 12, wherein the releasable and adjustable engaging means are intermeshing hook and loop members.

14. The holder of claim 13, wherein an outer surface of each support strap is provided with the loop members and the hook members are provided on both sides of a pair of tabs which are each releasably attachable to the folded portion and another portion of the support strap.

15. A method of applying a nasal dressing holder to a patient comprising the steps of:
providing a nasal dressing holder, the holder having an elastic central band sized to fit under the patient's nostrils, a pair of inelastic support straps having first ends attached to opposite ends of the central band and being sized to lie against the patient's cheeks, a pair of elastic ear loops, one attached to a second end of each strap and sized to encircle the patient's ears, and means for releasably adjusting the length of each strap;
placing a nasal dressing against or in the patient's nostrils;
placing the central band over the dressing and below the patient's nostrils;
placing the straps against the patient's cheeks and the loops around the patients's ears; and
adjusting the tension applied by the band to the dressing by adjusting the length of the straps.

16. The method of claim 15, further comprising:
replacing the dressing by pulling the band away from the nostrils, removing the dressing and inserting a new dressing, without removing the holder from the patient.

17. The method of claim 15, further comprising:
replacing the dressing by removing one or both of the loops from the patient's ears, removing the dressing and inserting a new dressing, and replacing the loops around the patient's ears.

18. The method of claim 15, wherein:
the strap-length adjusting means comprising a folded portion at the second end of each support strap in which a portion of the ear loop is positionable, and means are provided for releasably and adjustably engaging the folded portion with another portion of the strap; and
wherein the dressing is replaced by releasing one or both of the folded strap portions to release the tension on the dressing, removing the dressing and inserting a new dressing, and reattching one or both of the folded strap portions to the support straps.

19. The method of claim 15, wherein:
the central band comprises a central loop and the strap-length adjusting means comprises a folded portion at the first end of each strap, in which a portion of the central loop is positionable, and means are provided for releasably and adjustably engaging the folded portion with another portion of the strap; and
wherein the dressing is replaced by releasing one or both of the folded strap portions to release the tension on the dressing, removing the dressing and inserting a new dressing, and reattching one or both of the folded strap portions to the support straps.

* * * * *